US010905462B2

(12) United States Patent
Ochoa (10) Patent No.: US 10,905,462 B2
(45) Date of Patent: Feb. 2, 2021

(54) OPHTHALMIC CANNULA AND RETAINING FEATURE THEREFOR

(71) Applicant: NOVARTIS AG, Basel (CH)

(72) Inventor: Francisco Javier Ochoa, Cudahy, CA (US)

(73) Assignee: Alcon Inc., Fribourg (CH)

( * ) Notice: Subject to any disclaimer, the term of this patent is extended or adjusted under 35 U.S.C. 154(b) by 144 days.

(21) Appl. No.: 16/032,441

(22) Filed: Jul. 11, 2018

(65) Prior Publication Data

US 2019/0053825 A1 Feb. 21, 2019

Related U.S. Application Data

(60) Provisional application No. 62/545,907, filed on Aug. 15, 2017.

(51) Int. Cl.
*A61B 17/34* (2006.01)
*A61B 17/30* (2006.01)
*A61B 17/00* (2006.01)
*A61F 9/007* (2006.01)

(52) U.S. Cl.
CPC .......... *A61B 17/3421* (2013.01); *A61F 9/007* (2013.01); *A61B 2017/00345* (2013.01); *A61B 2017/308* (2013.01); *A61B 2017/348* (2013.01); *A61B 2017/3445* (2013.01)

(58) Field of Classification Search
CPC .......... A61B 17/3421; A61B 2017/308; A61B 2017/348; A61F 9/007; A61F 9/0017
See application file for complete search history.

(56) References Cited

U.S. PATENT DOCUMENTS

| | | |
|---|---|---|
| 5,607,391 A | 3/1997 | Klinger |
| 5,613,954 A | 3/1997 | Nelson |
| 5,817,099 A | 10/1998 | Skolik et al. |
| 5,820,600 A | 10/1998 | Carlson |
| 5,902,264 A | 5/1999 | Toso |
| 6,159,200 A | 12/2000 | Verdura |
| 6,524,238 B2 | 2/2003 | Velikaris |
| 6,616,632 B2 | 9/2003 | Sharp et al. |
| 8,062,260 B2 | 11/2011 | McCawley |
| 8,277,418 B2 | 10/2012 | Lopez |
| 8,292,853 B2 | 10/2012 | Hart |
| 8,298,188 B2 | 10/2012 | Okoniewski |
| 8,343,047 B2 | 1/2013 | Albrecht |
| 8,343,106 B2 | 1/2013 | Lopez |

(Continued)

FOREIGN PATENT DOCUMENTS

WO WO2009124406 A1 10/2009

OTHER PUBLICATIONS

Hip Arthroscopy. Product guide. STRYKER, 2011.

*Primary Examiner* — Katrina M Stransky
*Assistant Examiner* — Raihan R Khandker (57) ABSTRACT

A cannula may include a tubular section having a distal end, a proximal end, and forming a passage, and an elastomeric membrane coupled to and encircling the tubular section. The cannula may also include a valve that is movable between an open condition and a closed condition to selectively provide access to the passage defined by the tubular section. When the tubular section is inserted into an eye during an ophthalmic surgery, a concave surface of the elastomeric membrane acts as a suction cup to retain the cannula device onto a surface of an eye.

9 Claims, 6 Drawing Sheets

(56) References Cited

U.S. PATENT DOCUMENTS

| | | |
|---|---|---|
| 9,730,834 B2 | 8/2017 | Charles |
| 9,956,053 B2 | 5/2018 | Diao |
| 10,543,018 B2 | 1/2020 | Okoniewski |
| 2008/0172009 A1 | 7/2008 | Attinger |
| 2008/0312662 A1 | 12/2008 | Hickingbotham |
| 2009/0192465 A1 | 7/2009 | Smith |
| 2009/0318866 A1 | 12/2009 | Ferrari |
| 2009/0326461 A1 | 12/2009 | Gresham |
| 2010/0057010 A1 | 3/2010 | Goeransson |
| 2012/0172668 A1 | 7/2012 | Kerns |
| 2016/0067083 A1* | 3/2016 | Lue ............... A61F 9/0017 606/107 |
| 2016/0213511 A1* | 7/2016 | Murakami ......... A61B 17/3421 |
| 2018/0353326 A1 | 12/2018 | Hallen |
| 2020/0022773 A1 | 1/2020 | Grueebler |

\* cited by examiner

OPHTHALMIC CANNULA AND RETAINING FEATURE THEREFOR

CROSS-REFERENCE TO RELATED APPLICATIONS

This application claims the benefit of U.S. Provisional Application No. 62/545,907, filed Aug. 15, 2017, the entire contents of which are incorporated by reference.

TECHNICAL FIELD

The present disclosure generally pertains to microsurgical instruments for ophthalmic procedures. More particularly, but not by way of limitation, the present disclosure pertains to retention features for ophthalmic cannulas.

BACKGROUND

Microsurgical instruments may be used by surgeons for removal of tissue from delicate and restricted spaces in the human body, e.g., in surgery on the eye, such as surgical procedures for removal of the vitreous body, blood, scar tissue, or the crystalline lens, or to repair retina detachments and treat retina diseases. Such instruments may include a control console and a surgical handpiece with which the surgeon dissects and removes the tissue. The handpiece may be a vitreous cutter probe, a laser probe, an ultrasonic fragmenter for cutting or fragmenting the tissue, an irrigation probe, an aspiration probe, or an illumination probe and may be connected to the control console by a long air-pressure (pneumatic) line and/or power cable, optical cable, or flexible tubes for supplying an infusion fluid to the surgical site and for withdrawing or aspirating fluid and cut/fragmented tissue from the site. The cutting, infusion, and aspiration functions of the handpiece may be controlled by a remote-control console that not only provides power for the surgical handpiece(s) (e.g., power provided to operate a reciprocating or rotating cutting blade or an ultrasonically vibrated needle), but may also control the flow of infusion fluid and provide a source of vacuum (relative to atmosphere) for the aspiration of fluid and cut/fragmented tissue. The functions of the console may be controlled manually by the surgeon, (e.g., through use of a foot-operated switch or proportional control).

During posterior segment surgery, the surgeon may use several handpieces or other types of instruments during the procedure. This procedure may require that these instruments be inserted into, and removed out of the incision. This repeated removal and insertion may cause trauma to the eye at the incision site. To address this concern, hubbed ophthalmic cannulas (hereinafter, hubbed ophthalmic cannulas may be referred to as simply "cannulas") were developed at least by the mid-1980s. These devices may include a narrow tube with an attached hub. The tube may be inserted into an incision in the eye up to the hub, which may act as a stop, preventing the tube from entering the eye completely. The hub may then be stitched to the eye to prevent inadvertent removal. Surgical instruments can be inserted into the eye through the tube, and the tube may protect the incision sidewall from repeated contact by the instruments. In addition, the surgeon may use the instrument, by manipulating the instrument when the instrument is inserted into the eye through the tube, to help position the eye during surgery.

Disadvantages of some earlier cannulas include the height by which the hub extended or projected from the surface of the eye, as well as the lack of the ability to control loss of intraocular pressure during instrument exchange or removal. Early cannulas lacked a feature to prevent escape of fluid from the eye during instrument removal. Earlier versions of these devices were described as "open to atmosphere," and, because the eye is a pressurized globe, an open to atmosphere design can result in aqueous or vitreous fluid leaking or streaming out of the entry cannula, especially at higher intraocular pressure (TOP). With some earlier cannulas, loss of intraocular pressure was prevented by the insertion of a plug or cap into the tube to seal the cannula and prevent the expression of fluid and tissue when the instrument was removed from the cannula. Insertion and removal of the plug was a time-consuming process that may require additional instrumentation as well as the assistance of other operating room personnel and was also believed to increase the risk of post-operative infection.

To address some of these concerns, closed cannula systems have been introduced. Generally, closed cannulas include an elastomeric material that covers an end of the cannula outside of the eye. The elastomeric material has a slit to allow instruments to pass therethrough. The slit also has dimensions small enough to prevent most of the intraocular fluid from leaking out during a surgical procedure. Closed cannulas of this type are typically referred to as valved cannulas.

Typically, a surgeon relies upon friction between an outer surface of the cannula and the sclera of the eye to maintain the cannula's position within the eye. However, during an exchange of the microsurgical instruments, there is a risk that the cannula may be inadvertently removed, which may cause injury to the patient. Previously, in order to ensure against inadvertent extraction or movement of the cannula, a surgeon would grasp a cannula hub with a pair of forceps during the instrument exchange, to maintain the position of the cannula. Such a practice requires an extra step in the surgical procedure, thereby increasing the length of surgery. In addition, this practice also requires an extra hand to hold the forceps.

U.S. Pat. No. 8,062,260, issued 22 Nov. 2011 and titled "Trocar Cannula Device with Retention Feature," describes a cannula with a retention feature formed on the stem, or tubular shaft, of the cannula.

SUMMARY

According to one aspect, the present disclosure is directed to a cannula for use in ophthalmic surgical procedures. The cannula may include a tubular section defining a passage and an elastomeric membrane coupled to and encircling the tubular section. The tubular section may include a proximal end and a distal end. The elastomeric membrane may be disposed at the proximal end of the tubular section and may include a first surface and a second surface. The second surface may define a concave surface adapted to engage a surface of an eye.

According to another aspect, the present disclosure is directed to a cannula for use in ophthalmic surgical procedures. The cannula may include a seal moveable between an open condition and a closed condition; a tubular section extending distally from the seal and defining a passage; and an elastomer membrane coupled to and at least partially encircling the tubular section. The tubular section may include a proximal end and a distal end. The seal may provide access to the passage when the seal is in the open condition and may inhibit access to the passage when the seal is in the closed condition. The elastomeric membrane may include a first surface disposed adjacent to the seal; a second surface opposite the first surface; and one or more suction-cup features disposed on the second surface, the suction-cup features configured to engage a surface of an eye when the distal end of the tubular cannula section is positioned in the eye.

The different aspects may include one or more of the following features. The elastomeric membrane may include an outer periphery having a circular shape. The elastomeric membrane may include an outer periphery and a tab disposed at or near the outer periphery of the elastomeric membrane. The elastomeric membrane may include an inner region disposed adjacent to the tubular section and an outer region opposite the inner region. The inner region may be thicker than the outer region. The elastomeric membrane may include an annular rib disposed on the second surface and encircling the tubular section at a distance intermediate the tubular section and an outer periphery of the elastomeric membrane. The elastomeric membrane may include a plurality of annular ribs disposed on the second surface and encircling the tubular section at distances intermediate the tubular section and an outer periphery of the elastomeric membrane. The elastomeric membrane may be friction-fit to the tubular section. The tubular section may include an annular lip. The annular lip may be positioned proximate to the proximal end of the tubular section and adjacent to the elastomeric membrane, and the annular lip may be operable to prevent movement of the elastomeric membrane along the tubular section towards the distal end thereof. The elastomeric membrane may be overmolded onto an outer surface of the tubular section. The elastomeric membrane may include a retention tab, and the tubular section may include a recess. The retention tab may be received into the recess to retain the elastomeric membrane at a selected position along a length of the tubular section. An annular section may be attached to and encircle the tubular section at the proximal end thereof. The annular section may be disposed adjacent to the elastomeric membrane, opposite the second surface of the elastomeric membrane, and the annular section may be positioned so as to be operable to press the elastomeric membrane against a surface of an eye when the distal end of the tubular section is positioned in the eye. The elastomeric membrane may include one or more suction-cup features disposed on the second surface. The suction-cup features may be configured to engage a surface of an eye when the distal end of the tubular section is positioned in the eye.

The different aspects may also include one or more of the following features. The elastomeric membrane may fully encircle the tubular cannula section, and the second surface may define a concave surface adapted to engage a surface of the eye. The elastomeric membrane may include a tab disposed at or near an outer periphery of the elastomeric membrane. The elastomeric membrane may be friction-fit to the tubular section. The tubular section may include an annular lip, and the annular lip may be positioned adjacent to the elastomeric membrane between the elastomeric membrane and the distal end of the tubular section. The annular lip may be operable to prevent movement of the elastomeric membrane along the tubular section towards the distal end thereof. The elastomeric membrane may be overmolded to the tubular section. The elastomeric membrane may include a retention tab. The tubular section may include a recess, and the retention tab may be received into the recess to retain the elastomeric membrane at a selected position along a length of the tubular section. An annular section may be attached to and encircle the tubular section at the proximal end thereof. The annular section may be disposed adjacent to the elas-tomeric membrane, opposite the second surface of the elastomeric membrane, and the annular section may be positioned so as to be operable to press the elastomeric membrane against a surface of an eye when the distal end of the tubular section is positioned in the eye.

It is to be understood that both the foregoing general description and the following drawings and detailed description are exemplary and explanatory in nature and are intended to provide an understanding of the concepts disclosed herein without limiting the scope of the present disclosure. In that regard, additional aspects, features, and advantages will be apparent to one skilled in the art from the following.

BRIEF DESCRIPTION OF THE FIGURES

For a more complete understanding of the concepts described herein, reference is made to the following description taken in conjunction with the accompanying drawings in which.

It is to be understood that both the foregoing general description and the following detailed description are exemplary and explanatory only and are intended to provide a further explanation of the concepts described herein.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The following is a detailed description of example cannula devices. In some instances, the described example cannula devices may include one or more features described in U.S. Pat. No. 8,062,260 B2, the entire contents of which are incorporated herein by reference. It will be appreciated, however, that the improvements described herein, and in particular the retention features detailed below, may be applied to valved cannulas, open cannulas, or closed cannulas, as well as to cannulas having features that otherwise differ from those illustrated and explained herein. Thus, although the concepts described herein, particularly the retention features described herein, are made in the context of valved cannulas, the scope of the disclosure is not so limited. Rather, these concepts are also applicable to other types of cannulas, including open cannulas, for example.

Figure 1:
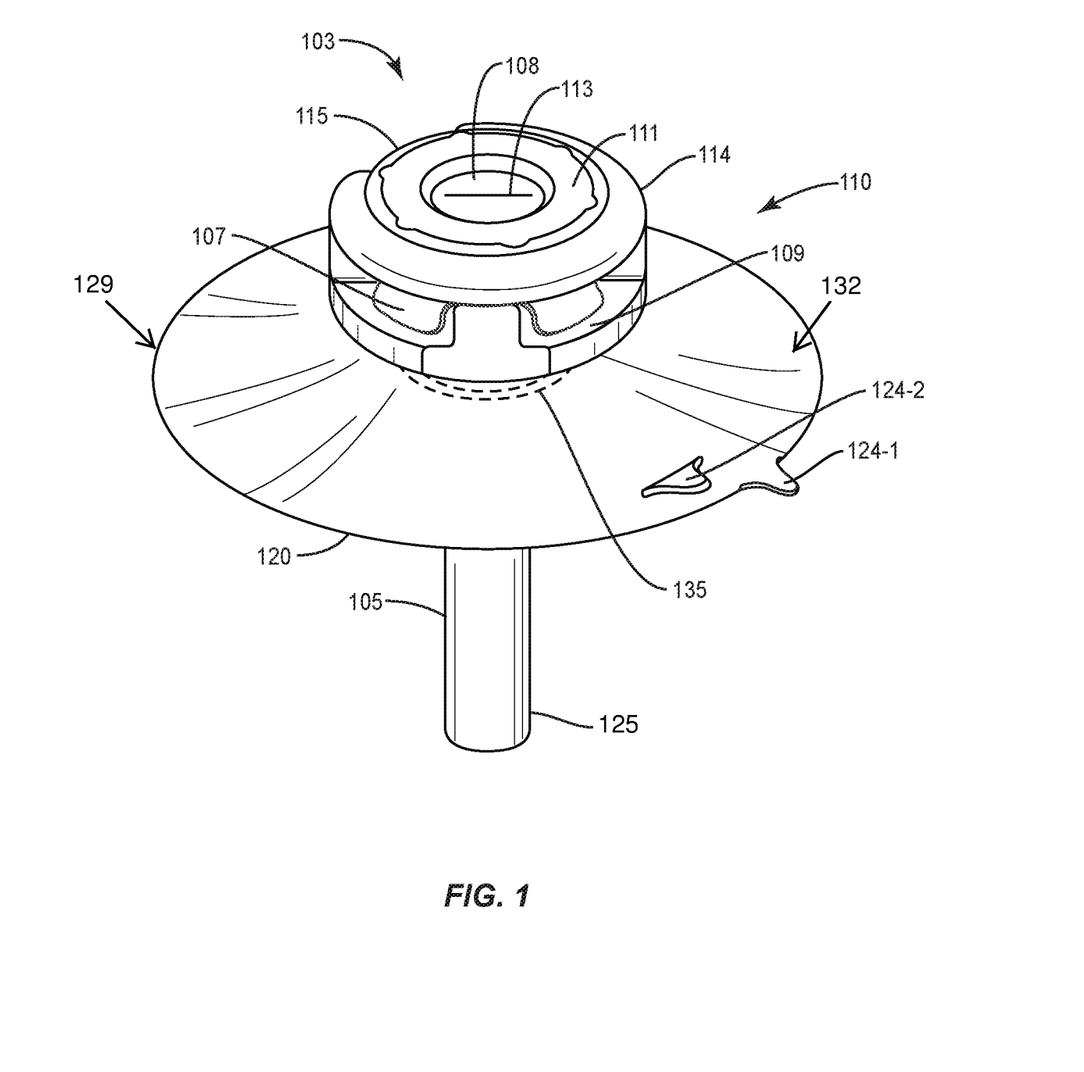
FIG. 1 is a perspective view of an example valved cannula.
Figure 2A:
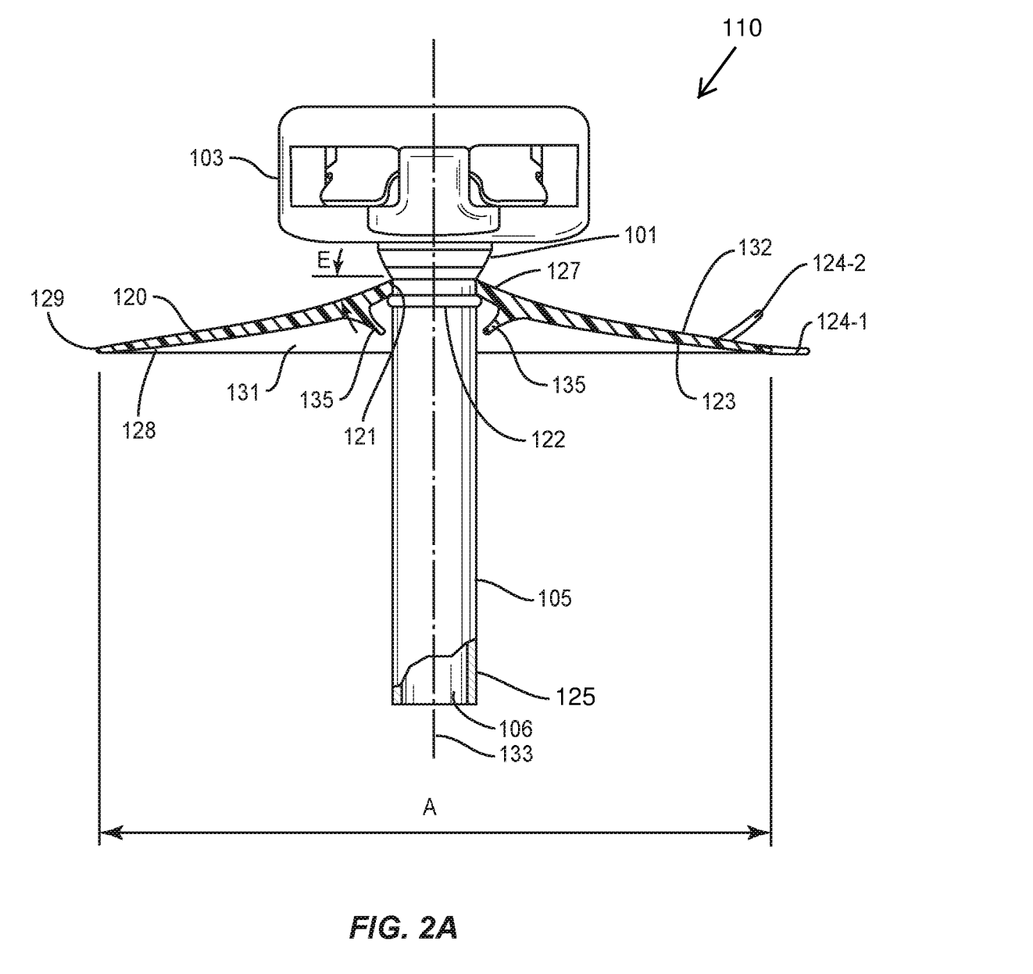
FIG. 2A is a partial cross-section of one example of the valved cannula of FIG. 1.

FIG. 1 illustrates an example valved cannula 110 that includes an overcap 103. The valved cannula 110 may be configured for insertion into an eye to facilitate insertion and removal of instruments during surgery. The valved cannula 110 includes a tubular section 105 that defines a passage 106 (as shown in FIG. 2A). Instruments may be passed through the passage 106 in order to gain access to an interior of an eye. The valve cannula 110 is insertable into the eye, such as through the sclera, conjunctiva, or other part of the eye so that a distal end of the valved cannula 110 is positioned within the interior of eye during use.

In some implementations, the valved cannula 110 may include an overcap 103, at a proximal end 101 of the tubular section 105 (as shown, for example, in FIG. 2A). The overcap 103 includes one or more slots 109. The valved cannula 110 may also include one or more tabs 107 configured to engage the corresponding slots 109. The tabs 107 are received into the corresponding slots 109 to retain the overcap 103 onto the tubular section 105. The valved cannula 110 illustrated in FIG. 1 includes four tabs 107, to engage four corresponding slots 109 formed in the overcap 103. Other methods of attaching the overcap 103 to the tubular section 105 are also contemplated. For example, in some implementations, the tubular section 105 may include one or more slots, and the overcap 103 may include one or more tabs to be received into the corresponding slots of the tubular section 105. In some implementations, the tubular section 105 may be attached to the overcap 103 via an adhesive, thermal bonding, interference fit, or any other bonding or joining method.

In some implementations, the valved cannula 110 may also include a seal 111. The seal 111 is coupled to the overcap 103, to form an overmolded valve. In the illustrated example shown in FIG. 1, the seal 111 is disposed at least partially between the tubular section 105 and the overcap 103. A surface 108 of the seal 111 is exposed at a proximal end 114 of the overcap 103. In some implementations, the exposed surface 108 of the seal 111 includes one or more slits 113 that open to allow passage of surgical instruments into and through the valved cannula 110. In the absence of a surgical instrument, the seal 111 remains closed to inhibit fluid flow through the valved cannula 110. Thus, the seal 111 is changeable between an open condition and a closed condition.

The valved cannula 110 illustrated in FIG. 1 further includes an elastomeric membrane 120. The elastomeric membrane 120 is coupled to and encircles the tubular section 105 at the proximal end 101 (proximal end 101 is obscured in FIG. 1, but is shown, for example, in FIGS. 2a-b) of the tubular section 105. As used here and elsewhere herein, the phrase "coupled to" is meant to convey that the elastomeric membrane 120 is attached to the remainder of the valved cannula 110 but not necessarily in a permanent fashion. The attachment of the elastomeric membrane 120 to the tubular section 105 may be, for example, by way of a friction fit between an opening 121 formed in a central portion of the elastomeric membrane 120 (as shown, for example, in FIG. 2A) and the tubular section 105. Alternatively, in some implementations, the elastomeric membrane 120 may be overmolded to the tubular section 105. Thus, in some implementations, the elastomeric membrane 120 may be coupled to the tubular section 105 via overmolding. The elastomeric membrane 120 may be coupled to the tubular section 105 in other way. For example, the elastomeric membrane 120 may be fitted to the tubular section 105 using one or more retention tabs and corresponding tab-receiving recesses, apertures, or grooves.

Figure 2B:
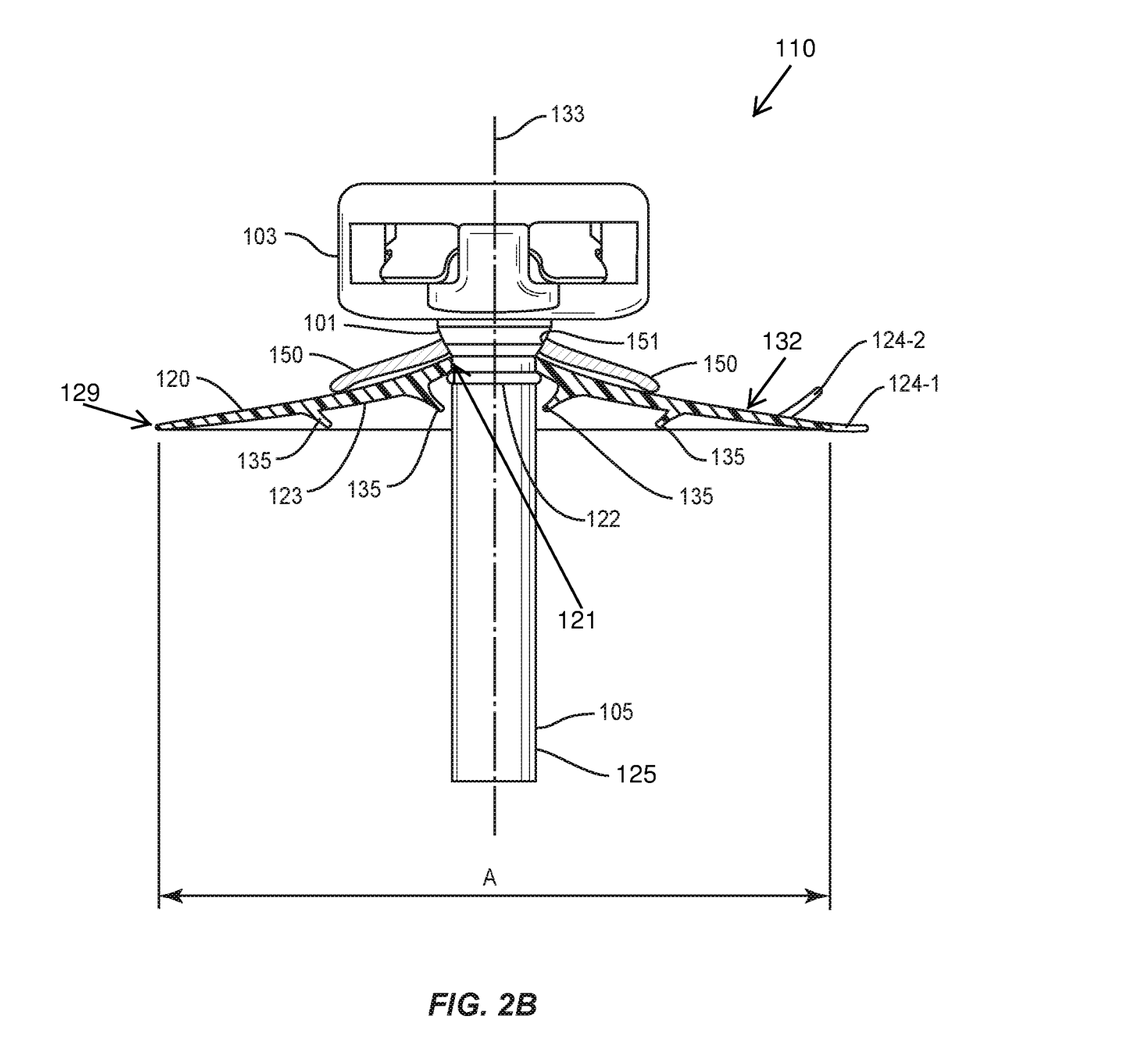
FIG. 2B is a partial cross-section of another example of the valved cannula of FIG. 1.

Another example valved cannula 110 is illustrated in FIGS. 2A and 2B. In this example, the tubular section 105 includes an annular lip 122 encircling the tubular section 105. The annular lip 122 is positioned closer to the distal end 125 of the tubular section 105 than the elastomeric membrane 120 and adjacent to the elastomeric membrane 120. The annular lip 122 prevents the elastomeric membrane 120 from sliding towards a distal end 125 of the tubular section 105.

Figure 3:
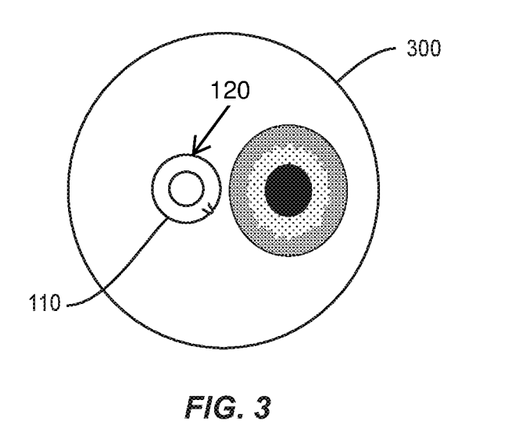
FIG. 3 is an illustration of an example valved cannula, positioned in an eye for an ophthalmic procedure.
Figure 4:
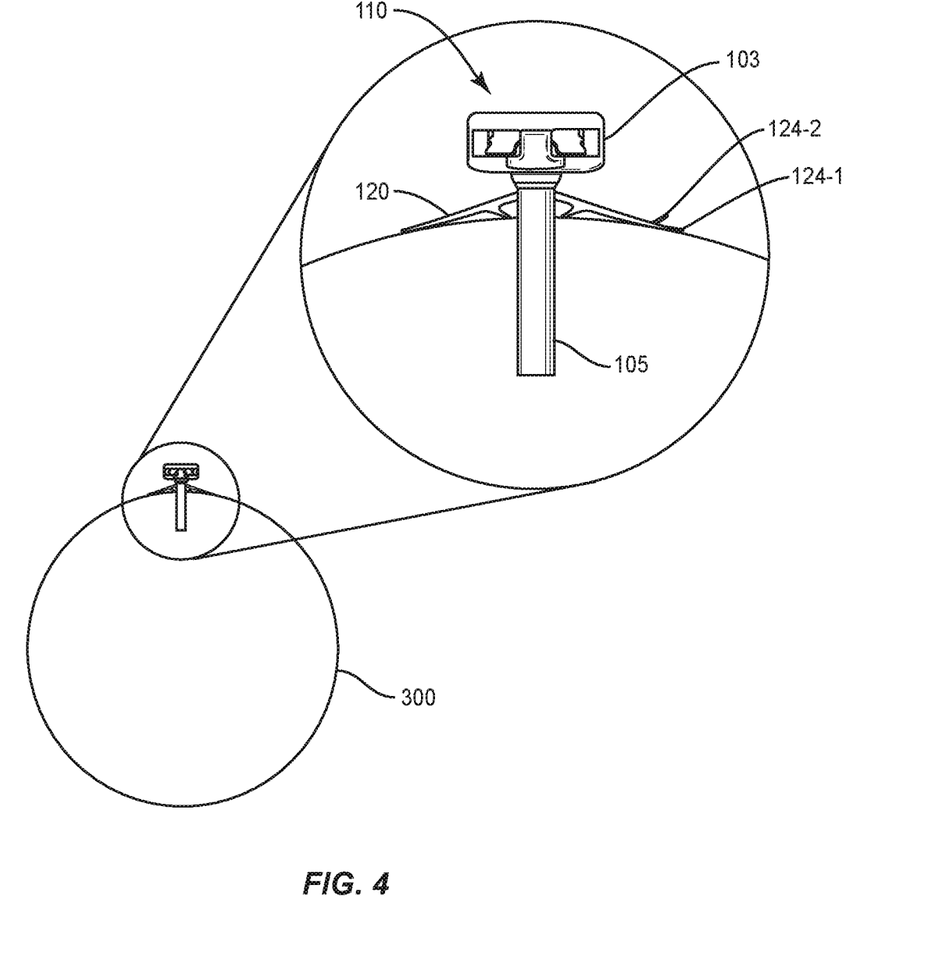
FIG. 4 is another view of an example valved cannula, positioned in an eye.

As seen in FIGS. 1, 2A, and 2B, the elastomeric membrane 120 includes a first surface 132 and a second surface 123 (second surface 123 is obscured in FIG. 1, but is shown, for example, in FIGS. 2a-b). The second surface 123 defines a concave surface that is disposed towards the distal end of the valved cannula 110. When the distal end of the valved cannula 110 is inserted into the eye, the elastomeric membrane 120 may be pressed against the sclera of the eye 300, as shown in FIGS. 3 and 4. As a result, the elastomeric membrane 120 acts as a suction cup, providing a retention force that resists removal of the valved cannula 110 from the eye 300. In the illustrated example of FIGS. 2a-b, the elastomeric membrane 120 is thicker at an inner region 127, closest to the tubular section 105, than in an outer region 128, farthest from the tubular section 105. As a result, flexibility of the elastomeric membrane 120 is greatest at an outer periphery 129, which improves the sealing performance of the elastomeric membrane 120 when the elastomeric membrane 120 is positioned against the eye.

As shown in FIGS. 1, 2A, and 2B, the outer periphery 129 of the example elastomeric membranes 120 is circular in shape. However, other shapes of the outer periphery 129 of the elastomeric membrane 120 are possible. Particularly, the outer periphery 129 may have any desired shape that allows the elastomeric membrane 120 to maintain a concave surface. The elastomeric membrane 120 has an outer diameter A. In the example shown in FIGS. 2A and 2B, the diameter A of the elastomeric membrane 120 is approximately 0.240 inches.

A depth of concavity of the elastomeric membrane 120 influences a retention force generated by the elastomeric membrane 120 when the elastomeric membrane 120 is pressed against the eye. When the elastomeric membrane 120 is pressed against the eye, air is pressed out of a volume 131 defined by the concavity of the elastomeric member 120 causing the elastomeric member 120 to form a vacuum between the elastomeric membrane 120 and the eye. The generated vacuum produces a retention force that retains the elastomeric membrane 120 against the eye. The magnitude of the retention force may be varied by varying a slope defined by the elastomeric membrane 120 relative to the tubular section 105. The slope may be defined by an angle E between a line perpendicular to a central axis 133 extending longitudinally through the tubular section 105 and a line tangent to a portion of the elastomeric membrane 120. As shown in FIG. 2A, the angle E defines a slope of the elastomeric membrane 120 near the opening 121 thereof. The slope of one or more regions of the elastomeric membrane 120 may be different from the slope of one or more different regions of the elastomeric membrane 120. Generally, the larger the angle E, the greater the retention force generated when the elastomeric membrane 120 is pressed against the eye.

In some implementation, the slope of the elastomeric membrane 120 may vary along a distance away from the tubular section 105, as shown, for example, FIGS. 2A and 2B. That is, in some implementations, the slope of the elastomeric membrane 120 may vary from the opening 121 to the outer periphery 129. The slope of one or more portions of the elastomeric membrane 120 may be varied in order to obtain a desired retention force.

The elastomeric membrane 120 includes diameter A. In some implementations, the diameter A may be 0.240 inches or any other desired size. The elastomeric membrane 120 may also include a maximum thickness. Generally, the maximum thickness of the elastomeric membrane 120 is located proximate to the opening 121. However, the maximum thickness of the elastomeric membrane 120 may be located anywhere along the elastomeric membrane 120. In some instances, the maximum thickness may be under about 0.125 inches in order to provide a desired level of flexibility. In other instances, the maximum thickness may be larger or smaller than the indicated value. For example, the maximum thickness may differ, in various implementations, depending on, for example, the overall size of the elastomeric membrane 120.

FIGS. 1, 2A, and 2B show the valved cannulas 110 as including pull tabs 124-1 and 124-2. The pull tabs 124-1 and 124-2 may be used to aid in releasing the elastomeric membrane 120 from the eye. For example, when a user desires to remove the valved cannula 110 from the eye, the user may grip the pull tab 124-1 or pull tab 124-2, such as, for example, with an tool, to gently pull the outer periphery 129 of the elastomeric membrane 120 away from the surface of the eye, thereby releasing the suction and removing the retention force. The pull tab 124-1 is disposed at the outer periphery 129 of the elastomeric membrane 120, while the pull tab 124-2 protrudes from the first surface 132 of the elastomeric membrane 120, near the outer periphery 129. Various implementations may include one or more of either or both types of these pull tabs.

Leakage from the eye 300 during the surgical procedure may occur at a location where the tubular section 105 penetrates the eye 300 (e.g., where the tubular section 105 penetrates the sclera of the eye 300). This leakage has the potential to impair the suction generated by the elastomeric membrane 120. Consequently, leakage at the site of penetration of the valved cannula 110 has the potential to diminish the ability of the elastomeric membrane 120 to remain retained onto the eye 300. In order to eliminate or reduce the potential for leakage, the elastomeric membrane 120 may include one or more annular ribs 135 disposed on the concave second surface 123 of the elastomeric membrane 120. The annular rib or ribs 135 may be disposed at a distance intermediate the opening 121 and the outer periphery 129 of the elastomeric membrane 120, as shown in FIGS. 2A and 2B. The annular ribs 135 act to seal off an area proximate to the wound, thereby preventing fluid from flowing outwardly from the wound and towards outer periphery 129 of the elastomeric membrane 120. In the example shown in FIG. 2B, the elastomeric membrane includes two annular ribs 135. The annular ribs 135 have tapered cross-sections, although one or more of the ribs 135 may have non-tapered cross-sections. In other implementations, the elastomeric member 120 may have a plurality of closely spaced annular ribs 135, with or without tapered cross sections, to improve both the retention performance of the elastomeric membrane 120 as well as to reduce or eliminate leakage from the wound into which the valved cannula 110 is inserted.

Figure 5A:
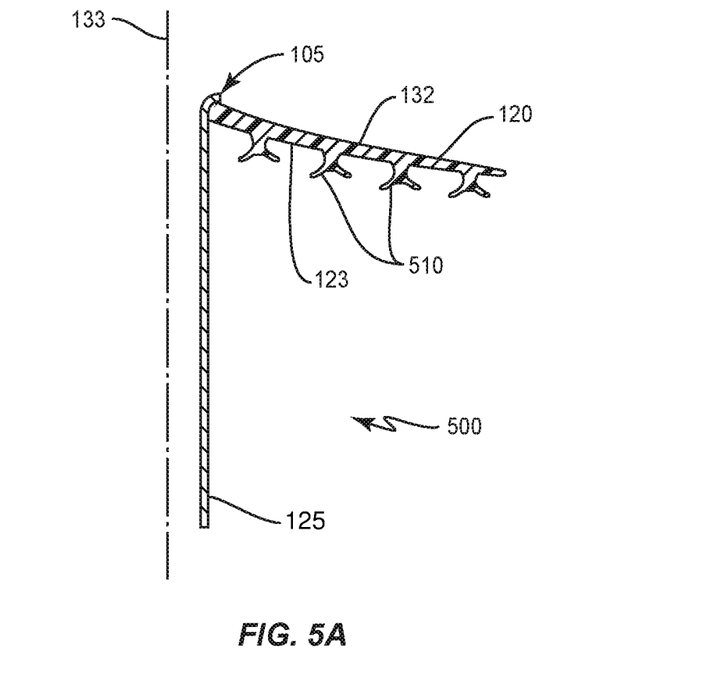
FIG. 5A is a cross-section illustrating a portion of another example valved cannula.
Figure 5B:
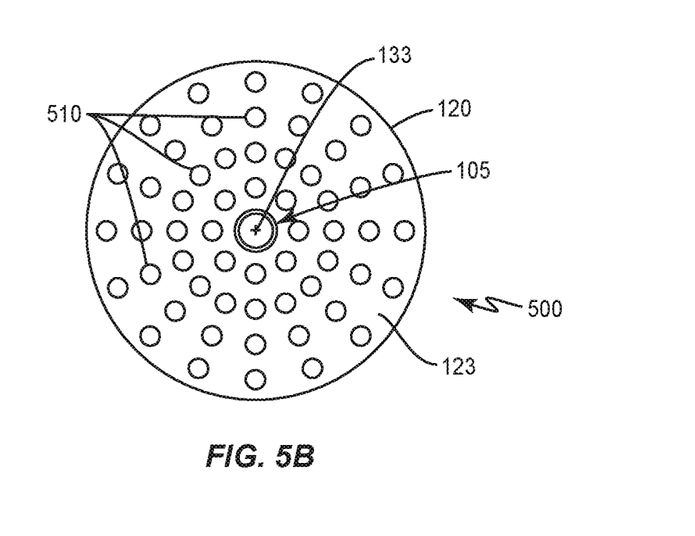
FIG. 5B is another view of the valved cannula of FIG. 5A.

FIGS. 5A and 5B illustrate another example elastomeric membrane 120 that may be incorporated into a valved cannula. FIG. 5A is a partial cross-sectional view of a tubular section 105 and elastomeric membrane 120 of an example valved cannula 500. FIG. 5B is an end view of the example valved cannula 500 of FIG. 5A. The illustrated elastomeric membrane shown in FIGS. 5A and 5B includes one or more suction-cup features 510 disposed on the second surface 123 of the elastomeric membrane 120. In some instances, the second surface 123 may be a flat surface or a curved surface. For example, in some instances, the second surface 123 may define a concave surface. In some instances, the suction-cup features 510 may be randomly positioned on the second surface of the elastomeric membrane 120. In other implementations, the suction-cup features 510 may be have an ordered arrangement on the second surface 123. For example, in some instances, the suction-cup features 510 may be organized in patterns over the second surface 123. These suction-cup features 510 are configured to engage the surface of the eye to generate a retention force that retains the valved cannula 500 onto the eye during use.

In some implementations, the suction-cup features 510, similar to those shown in FIG. 5A, may be distributed across the entirety of the second surface 123 of an elastomeric membrane 120. Thus, in some implementations, the suction-cup features 510 may be distributed along an entire 360 angular range of the second surface 123, as measured about the axis 133. In other implementations, the suction-cup features 510 may be distributed over only a selected or discrete portion or portions of the lower surface 123 of the elastomeric membrane 120. In some implementations, the elastomeric membrane 120 may also include one or more annular ribs similar to the annular ribs 135 described above. In other implementations, annular ribs may be omitted. In some implementations that include both an annular rib and suction-cup features, a portion of the second surface 123 circumscribed by an annular rib may exclude any suction-cup features, while one or more portions or the entire remainder of the second surface 123 outside of the area circumscribed by the annular rib may include one or more suction-cup features.

The elastomeric membrane 120 of the example valved cannulas illustrated herein fully surrounds the tubular section 105. In other instances, such as one or more of the implementations that include one or more suction-cup features 510, the elastomeric membrane 120 may only partially encircle the tubular section 105, such that the elastomeric membrane 120 forms one or more freely-extending or cantilevered flaps extending from the tubular cannula section 105. The freely-extending flap or flaps may include one or more suction-cup features 510 disposed on the second surface 123 of the flap or flaps.

Some implementations of a valved cannula may include an annular section. Referring again to FIG. 2B, the example valved cannula 110 also includes an annular section 150 that is disposed adjacent to the elastomeric membrane 120 between the elastomeric member 120 and the overcap 103. The annular section 150 is disposed at the proximal end 101 of the tubular section 105. The annular section 150 forms a conical structure that surrounds the tubular section 105. The annular section 150 includes a central opening 151 through which the tubular section 105 extends. During insertion of the valved cannula 110 into an eye, the annular section 150 provides increased rigidity to an inner portion of the elastomeric membrane 120. This increased rigidity improves engagement of the elastomeric membrane 120 and the outer surface of the eye. As a result, the annular section 150 is believed to improve the retention of the elastomeric membrane 120 (and, hence, the valved cannula 110) to the eye.

A cross-section of an example annular section 150 is illustrated in FIG. 2B. In some instances, the annular section 150 may completely encircle the tubular section 105. In other implementations, the annular section 150 may only partly encircle the tubular section 105. For example, in some instances, the annular section 150 may include one or two or more discrete sections freely extending from the tubular section 105. It will be appreciated that an annular section, similar to the annular section 150, may be included with the example valved cannulas shown in FIGS. 5A and 5B.

Figure 6:
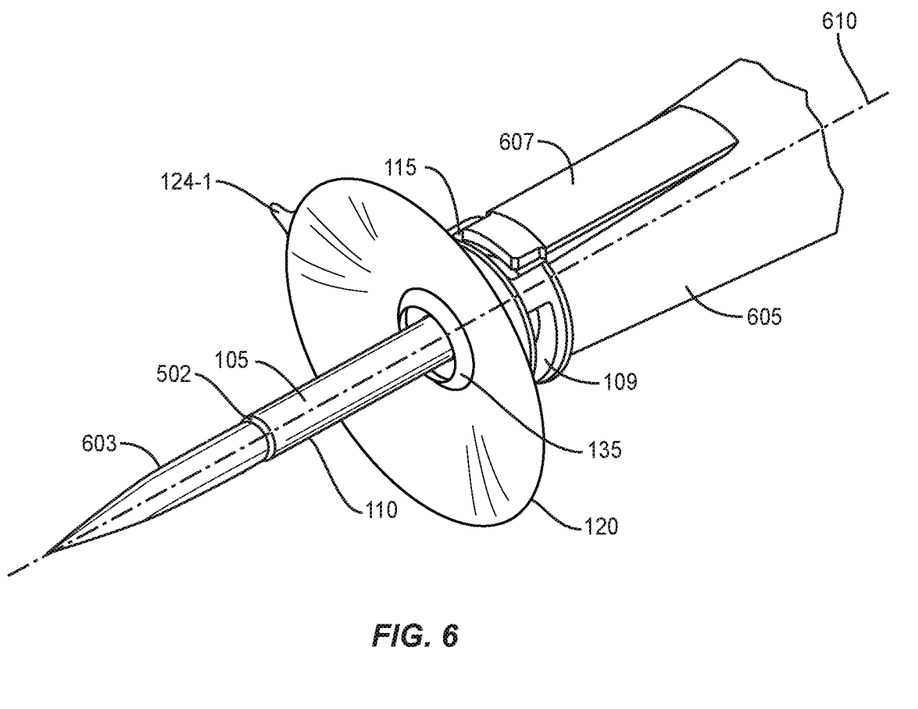
FIG. 6 illustrates an example valved cannula installed on a trocar inserter.

FIG. 6 illustrates an example the cannula device within the scope of the disclosure disposed on a trocar inserter. The trocar inserter includes a trocar blade 603 attached to a handle 605. In some embodiments, the handle 605 may be made of plastic, and the trocar blade 603 may be made of stainless steel. Other materials are also contemplated. The trocar blade 603 extends distally beyond the distal end 125 of the tubular section 105 and includes sharp edges to pierce an eye (e.g., pierce a hole through the sclera and into the vitreous body) for insertion of the valved cannula 110. Although the illustrated example includes two sharp edges, other implementations of the trocar blade 603 may include fewer or additional blades. In some implementations, a guide 607 is received into the guide slot 115 of the valved cannula 110 in order to inhibit rotation of the valved cannula 110 relative to the handle 605, such as during insertion of the valved cannula 110 into the eye. The guide 607 releasably engages the guide slot 115 such that, when the trocar inserter is withdrawn from the valved cannula 110, the guide 607 does not remove the valved cannula 110 from the eye. For example, the guide 607 may frictionally engage the guide slot 115 with a friction force that is insufficient to remove the valved cannula 110 from the eye. For example, the frictional force resulting from the engagement of the guide slot and the guide 607 may be less than a frictional force exerted by the eye on the external surfaces of the valved cannula 110 when the valved cannula 110 is inserted in the eye.

While the guide 607 is depicted as including a tab that is receivable into the guide slot 115, other interlocking features are also contemplated. For example, the guide 607 and guide slot 115 may include different interlocking features (such as a ring and a rod) or may include other interlocking components, such as interacting or interlocking magnets (e.g., one magnet included on each of the handle 605 and the overcap 103), engaging O-rings (e.g., one O-ring included on each of the handle 605 and overcap 103), etc. In some implementations, engagement of the guide 607 and the guide slot 115 may prevent rotation between the valved cannula 110 and the handle 605 so that any angular movement of the handle 605 about a longitudinal axis 610 of the handle 605 is transmitted to the valved cannula 110. This anti-rotation interaction between the handle 605 and the valved cannula 110 provides a user, such as a vitreoretinal surgeon, angular control of the valved cannula 110 relative to the handle 605 during insertion of the valved cannula 110 into the eye.

Persons of ordinary skill in the art will appreciate that the implementations encompassed by the present disclosure are not limited to the particular exemplary implementations described above. In that regard, although illustrative implementations have been shown and described, a wide range of modifications, changes, and substitutions is contemplated in the foregoing disclosure. It is understood that such variations may be made to the foregoing without departing from the scope of the present disclosure. Accordingly, it is appropriate that the appended claims be construed broadly and in a manner consistent with the concepts encompassed by the present disclosure.

What is claimed is:

1. A cannula for use in ophthalmic surgical procedures comprising:
   a tubular section defining a passage, the tubular section comprising:
      a proximal end; and
      a distal end;
   an elastomeric membrane coupled to and encircling the tubular section at the proximal end of the tubular section, the elastomeric membrane comprising:
      a first surface; and
      a second surface opposite the first surface, the second surface defining a concave surface adapted to engage a surface of an eye;
   wherein the elastomeric membrane comprises an outer periphery having a circular shape;
   wherein the elastomeric membrane comprises a pull tab that is not on the outer periphery but protrudes from the first surface at an angle that positions the pull tab over at least a portion of the first surface;
   wherein the pull-tab is configured to be grabbed by a user to release a suction force between the second surface and the surface of the eye when the second surface is in contact with the surface of the eye.

2. The cannula of claim 1, wherein the elastomeric membrane further comprises an inner region disposed adjacent to the tubular section and an outer region opposite the inner region, the inner region being thicker than the outer region.

3. The cannula of claim 1, wherein the elastomeric membrane further comprises an annular rib disposed on the second surface and encircling the tubular section at a distance intermediate the tubular section and an outer periphery of the elastomeric membrane.

4. The cannula of claim 1, wherein the elastomeric membrane further comprises a plurality of annular ribs disposed on the second surface and encircling the tubular section at distances intermediate the tubular section and the outer periphery of the elastomeric membrane.

5. The cannula of claim 1, wherein the elastomeric membrane is friction-fit to the tubular section.

6. The cannula of claim 1, wherein the tubular section comprises an annular lip, the annular lip positioned proximate to the proximal end of the tubular section and adjacent to the elastomeric membrane, the annular lip operable to prevent movement of the elastomeric membrane along the tubular section towards the distal end thereof.

7. The cannula of claim 1, wherein the elastomeric membrane is overmolded onto an outer surface of the tubular section.

8. The cannula of claim 1, further comprising an annular section attached to and encircling the tubular section at the proximal end thereof, the annular section disposed adjacent to the elastomeric membrane, opposite the second surface of the elastomeric membrane, the annular section positioned so as to be operable to press the elastomeric membrane against the surface of the eye when the distal end of the tubular section is positioned in the eye.

9. The cannula of claim 1, wherein the elastomeric membrane comprises one or more suction-cup features disposed on the second surface, the suction-cup features configured to engage the surface of the eye when the distal end of the tubular section is positioned in the eye.

\* \* \* \* \*